United States Patent [19]
Deneke et al.

[11] Patent Number: 4,966,855
[45] Date of Patent: Oct. 30, 1990

[54] NEW REDOX INDICATORS

[75] Inventors: Ulfert Deneke, Rimbach-Zotzenbach; Werner Güthlein, Mannheim; Wolfgang Weckerle, Grünstadt; Hans Wielinger, Weinheim, all of Fed. Rep. of Germany

[73] Assignee: Boehringer Mannheim GMBH, Manheim, Fed. Rep. of Germany

[21] Appl. No.: 751,367

[22] Filed: Jul. 2, 1985

[30] Foreign Application Priority Data

Jul. 7, 1984 [DE] Fed. Rep. of Germany ....... 3425118

[51] Int. Cl.$^5$ .................. G01N 33/72; C12Q 1/28; C07D 263/30
[52] U.S. Cl. ................... 436/66; 436/135; 436/904; 422/58; 435/28; 435/807; 548/235; 546/23; 546/94; 546/172; 546/174; 546/176; 544/82; 544/84; 544/85; 544/87; 544/137
[58] Field of Search ................ 548/235; 436/66, 95, 436/135, 904; 422/58; 544/37, 82, 84, 85, 87; 435/28, 807; 546/172, 174, 176, 94, 23

[56] References Cited

U.S. PATENT DOCUMENTS

| | | |
|---|---|---|
| 3,630,957 | 12/1971 | Rey et al. .............................. 252/408 |
| 4,089,747 | 5/1978 | Brushi ..................................... 195/99 |
| 4,220,713 | 9/1980 | Rittersdorf et al. ................... 435/14 |
| 4,312,834 | 1/1982 | Vogel et al. ............................ 422/56 |
| 4,477,575 | 10/1984 | Vogel et al. ............................ 436/170 |
| 4,604,264 | 8/1986 | Rothe et al. ............................ 422/56 |

FOREIGN PATENT DOCUMENTS 1407873 10/1975 United Kingdom .................. 435/14

Primary Examiner—Richard L. Raymond
Assistant Examiner—Raymond Covington
Attorney, Agent, or Firm—Felfe & Lynch

[57] ABSTRACT

The invention provides new redox indicators and uses for these redox compounds (I):

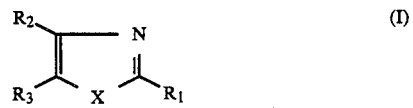

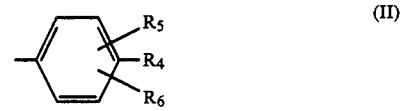

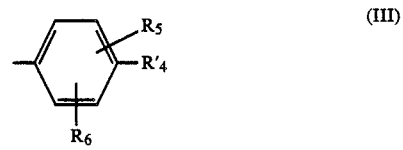

Wherein X is oxygen or sulphur, $R_1$ is julolidine or tetrahydroquinoline, which can carry an alkyl radical on the nitrogen atom which, in turn, can be substituted by a sulphuric, phosphonic or carboxylic acid residues, or is (II); wherein $R_4$ is hydroxyl or a mono- or dialkylated amino group, $R_5$ and $R_6$, which can be the same or different, are hydrogen, alkyl or alkoxy, $R_2$ is hydrogen or alkyl, julolidine or tetrahydroquinoline, which can carry an alkyl on the nitrogen atom which alkyl can be substituted by sulphuric, phosphonic or carboxylic acids, or is III; wherein $R_5$ and $R_6$ are the same as in $R_1$ and $R'_4$ is hydroxyl, an amino or a mono-or dialkylated amino group, whereby the alkyl radicals can be substituted one or more times by hydroxyl, alkoxy, halogen, morpholine or a sulphuric, carboxylic or phosphonic acid residue, which acids can also be esterified, and $R_3$ is the same as $R_2$ or is an alkyl substituted by hydroxyl, alkoxy, dialkylamino or phenyl, or is cycloalkyl, phenyl or pyridyl; as well as the salts thereof.

7 Claims, No Drawings

NEW REDOX INDICATORS

The present invention is concerned with new redox indicators, with the preparation thereof and with reagents containing them.

The reaction of hydrogen peroxide with oxidation indicators catalysed by peroxidase or of peroxidate-active substances plays a special part in analytical chemistry because, apart from the detection of hydrogen peroxide and peroxidase, it also permits the determination of a series of substances which react with oxygen and a series of materials with the formation of hydrogen peroxide. In the following, some of these materials are listed by way of example and the corresponding oxidases are mentioned in brackets: glucose (glucose oxidase), galactose (galactose oxidase), L-amino acids (L-amino acid oxidase), cholesterol (cholesterol oxidase), uric acid (uricase), sarcosine (sarcosine oxidase), glycerol (glycerol oxidase) and pyruvate (pyruvate oxidase).

As a detection reaction for peroxidases, the method is especially useful for the determination of haemoglobin.

These are, in particular, reactions which are of great importance in medical diagnosis and in foodstuff chemistry.

The detection reactions are carried out either in a cuvette or with the help of dry reagents. Quantification thereby takes place in photometers via a transmission measurement, with remission photometers via remission measurement or with the help of comparative colors by visual comparison.

The use of dry reagent carriers, i.e. absorbent or swellable carriers, which are impregnated with the reagents or in which the reagents are incorporated via another step and on which, after moistening with the substrate, the detection reaction takes place, has recently achieved ever increasing importance. The adjuvants permit, by means of simple handling, with a simultaneous great saving of time, a decisive rationalization of the analyses in question. The stimulus to develop dry reagents with which it is possible to operate with undiluted samples gives the developer the problem, with regard to the choice of the indicator or indicator system to be used, that serum or plasma (hereinafter referred to as serum) considerably disturbs the detection reaction. These disturbances make themselves noticeable especially when it is necessary to detect the substrates or enzyme activities via coupled reaction steps. As examples of substrates, there are here mentioned the detection of creatinine and uric acid and, as examples of activity determinations of enzymes, the determination of creatine kinase, glutamate-oxalacetate transaminase (GOT) and glutamate-pyruvate transaminase (GPT).

From the literature, there are known numerous compounds which can be used as indicators for the detection of hydrogen peroxide with peroxidase as catalyst. Such indicators include benzidine and benzidine derivatives, various phenols, polyphenols, for example, guaiac resin, leuko dyestuffs, for example leuko malachite green, dichlorophenolindophenol, aminocarbazoles, triarylimidazoles and 2,2'-azino-di-[3-ethylbenzthiazole-6-sulphonic acid], as well as dyestuffs which result as coupling products of the oxidative coupling of aminoantipyrine or related substances with phenols, naphthols, aniline derivatives and other coupling components.

In the case of the detection of hydrogen peroxide in undiluted serum samples, the above-mentioned known indicators display more or less great disturbances due to reactions with other components of the serum which falsify a higher or mostly lower concentration of the substrate to be detected. Relatively less disturbed are some triarylimidazoles, such as are described in Federal Republic of Germany Patent Specification No. 27 35 690. However, these imidazoles are only stable in the acidic pH range and, as experiments have shown, are, in the case of transfer into a weakly acidic to weakly alkaline pH range, such as is necessary in the case of almost all enzymatic reactions, i.e. when they are present as free bases, spontaneously oxidised by atmospheric oxygen. Therefore, a working up to functional dry reagents with these indicators is only possible when they are embedded in a protective colloid, for example gelatine. However, this can only be carried out in special cases.

Therefore, it is an object of the present invention to provide coloured material formers for the detection reaction of hydrogen peroxide or of peroxidate-active substances which do not react with the disturbing substances contained in serum, are not spontaneously oxidised by atmospheric oxygen in the weakly acidic to weakly alkaline range and thus can be used not only in a cuvette test but also in all matrices which can be used for dry reagent carriers.

Thus, according to the present invention, there are provided oxazole and thiazole derivatives of the general formula:

 (I)

wherein X is an oxygen or sulphur atom, $R_1$ is a radical of the general formula:

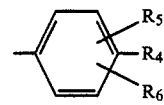

in which $R_4$ is a hydroxyl group or a mono- or dialkylated amino group, $R_5$ and $R_6$, which can be the same or different, are hydrogen atoms, alkyl or alkoxy radicals, which can be substituted by a carboxyl group or a julolidine or tetrahydroquinoline radical, which can carry an alkyl radical on the nitrogen atom, which in turn can be substituted by a sulfo, phosphonic acid or carboxylic acid residue, $R_2$ is a hydrogen atom or an alkyl, julolidine or tetrahydroquinoline radical, which can carry an alkyl radical on the nitrogen atom which, in turn, can be substituted by a sulfo, phosphonic acid or carboxylic acid residue, or a radical of the general formula:

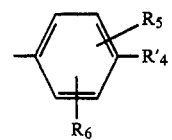

in which $R_5$ and $R_6$ have the same meanings as given in the definition of $R_1$ and $R'_4$ is a hydroxyl or amino group or a mono- or dialkylated amino group, whereby the alkyl radicals can be substituted one or more times by hydroxyl, alkoxy, halogen, morpholine, sulfo, carboxylic acid or phosphonic acid, which can also be esterified, and $R_3$ has the same meaning as $R_2$ or can be an alkyl radical which is substituted by hydroxyl, alkoxy, dialkylamino or phenyl, or is a cycloalkyl, phenyl or pyridyl radical; as well as the salts thereof.

The expression alkyl in the definition of the substituents $R_2$, $R_3$, $R_4$, $R'_4$, $R_5$ and $R_6$ means radicals with 1 to 6 and preferably 1–4 carbon atoms, the methyl, ethyl, propyl, butyl and tert.-butyl radicals being preferred. The amino groups of the phenyl substituents are, as a rule, substituted by alkyl radicals with 1 to 4 carbon atoms, methyl being preferred. All alkyl radicals can, in turn, be substituted one or more times by halogen, hydroxyl, methoxy, carboxyl, a sulfo or phosphonic acid residue, which can also be esterified by methanol or ethanol, or by a morpholino radical.

The tetrahydroquinoline radical is a 1,2,3,4-tetrahydroquinoline radical and can carry on the nitrogen atom an alkyl radical with 1 to 6 carbon atoms, preferably a methyl radical. These alkyl radicals can, in turn, carry a carboxyl, phosphonic acid or sulphonic acid residue.

Cycloalkyl radicals in the definitions of the substituent $R_3$ are radicals with 3 to 7 carbon atoms, the cyclopropyl, cyclopentyl and cyclohexyl radicals being preferred.

By alkoxy radicals in the definitions of the substituents $R_2$, $R'_4$, $R_5$ and $R_6$, alone or as substituents of alkyl radicals, are to be understood radicals with 1 to 6 and preferably 1 to 4 carbon atoms, methoxy, ethoxy and propoxy radicals being preferred.

Preferred substituents $R_1$, $R_2$ and $R_3$ include, for example, 3,5-dimethoxy-4-hydroxyphenyl, 3,5-di-(-tert.-butyl)-4-hydroxyphenyl, 4-dimathylaminophenyl, 9-julolidino, as well as 6-N-methyl-1,2,3,4-tetrahydroquinolino, whereby the alkyl substituents can carry carboxyl, phosphonic acid or sulfo groups. Furthermore, $R_2$ and $R_3$ can also preferably signify methyl. Apart from the above-mentioned radicals, $R_3$ means especially hydrogen, n-butyl, tert-butyl, 3-methoxypropyl, 4-methoxybutyl, 5-methoxypentyl, cyclohexyl, phenyl, benzyl, hydroxymethyl, pyridyl or dimethylaminomethyl.

The sulfo, phosphonic acid and carboxylic acid residues with which alkyl radicals are preponderantly substituted, serve especially for improving the solubility.

The indicators of general formula I can be incorporated into all known detection systems.

With the indicators there can be produced tests which are measured in a cuvette. For this purpose, the indicator, together with peroxidase, the enzyme or enzymes required for the detection of the particular parameter, other reagents and a buffer system and possibly wetting agents and other adjuvants are lyophilised, mixed as a powder or pressed into tablets. The reagent mixture thus obtained is, before use, dissolved in water and the reagent solution is thus prepared. After the addition of the sample (substrate solution, enzyme solution, serum or plasma), the resultant color is measured in a photometer and the particular concentration or enzyme activity calculated via the molar extinction coefficients and the added volume of reagent or sample. Not only kinetic but also end point measurements are possible.

In the same way, the indicators, together with peroxidase, the reagent or reagents necessary for the particular parameter to be detected or other enzymes, a buffer system, possibly wetting agents and other adjuvants can be impregnated on to absorbent reagent carriers, such as papers, fleece or the like. For this purpose, one or more impregnation solutions can be prepared in the form of aqueous or organic or mixed solutions, depending upon how the reagents or adjuvants dissolve, and carriers are impregnated or sprayed with these solutions. Subsequently, the carriers are dried. The reagent carriers thus obtained can be used as rapid diagnostics for the direct determinations of component materials of, for example, body fluids. The body fluid is thereby applied directly to the reagent carrier or the reagent carrier is dipped into the body fluid. By comparison of the resultant colour with comparative colors, a semiquantitative determination is possible. By means of remission photometric processes, a quantitative evaluation is also possible. It is also possible to prepare a reagent solution by eluting with water or buffer the reagents impregnated, as above described, on a paper or fleece, with which eluted solution substrates and enzymes are determined in a cuvette using a photometer as described hereinbefore (cf. Federal Republic of Germany Patent Specification No. 2,301,999).

Another possibility for the use of the indicators according to the present invention is the use thereof in reagent films for the quantitative determination of enzymes or substrates by means of a remission photometer. In this case, the indicator, together with the other necessary reagents and adjuvants, is worked up to give a reagent film, for example according to the processes described in Federal Republic of Germany Patent Specifications Nos. 1,598,153 and 2,910,134.

Furthermore, the indicators according to the present invention can also be successfully combined with stabilisers such as are described, for example, in Federal Republic of Germany Patent Specification No. 2,716,060. These stabilisers, which are 1-aryl semicarbazides, result in the finished tests being insensitive to the influence of light and, with larger amounts, the function curves of the remission-photometric measurements can be modulated.

As mentioned above, the indicators according to the present invention can be incorporated into all conventional reagent carriers, i.e. absorbent carriers, such as filter papers, fleece and the like, or into swellable or absorbent reagent films (see Federal Republic of Germany Patent Specifications Nos. 1,598,153; 2,910,134 and 3,247,608).

However, since they are preferably to be used for the detection of enzymes and substrates in serum, in FIGS. 1–4 of the accompanying drawings, there are shown in cross-section a series of devices which permit, according to Federal Republic of Germany Patent Specification No. 3,029,579, on the one hand, serum or plasma for the test to be separated from whole blood and, on the other hand, on the basis of a special construction of the reagent and adjuvant layers, permit a tempering, pre-reaction and directed starting of the main reaction.

In detail, the devices are constructed as follows:

FIG. 1.

On to an inert carrier film 12 is fixed a layer 4 consisting of glass fibres which serves, on the one hand, for the transport of the serum and, on the other hand, for the separation of serum and erythrocytes. Partially covering this layer 4 is a further separating zone 5 of glass fibres fixed by means of a fixing mesh 6. Whole blood is applied to this mesh 6 which is separated in the zone 5 or zone 4 into serum and erythrocytes, the latter being retained, so that only serum passes over into the left-hand region of the zone 4. Laterally of the zone 4, via an adhesive connection 13, there is fixed a thin synthetic resin fabric 3, as well as a carrier film 1 consisting of a transparent synthetic resin. Under the carrier film 1, there is, in turn, fixed a reagent zone 2 which consists either of a swellable or absorbent film and in which are incorporated the reagents necessary for the reaction. A part of the reagents, especially those necessary for a pre-reaction, can also be contained in zone 4. By pressure on the carrier film 1, the reaction is started after the serum has completely filled the zone 4, which, by means of the pressure contact, penetrates through the mesh 3 into the reagent zone 2 and moistens this uniformly. If additional atmospheric oxygen is necessary for the reaction, after moistening through of the zone 2, the device can again be separated. The reaction is observed through the carrier film 1 and evaluated on the basis of the coloration in zone 2.

FIG. 2.

The construction of the zones serving for obtaining the serum correspond to FIG. 1. In order to ensure a separation of the reagents, which possibly are not storage-stable in the presence of one another, two reagent papers 8 and 9 are provided which, together with the protective covering film 7, are connected via the adhesive point 13 to the carrier film 12. Here again, after saturation of the zone 4 with serum by pressure on the covering film 7, a liquid contact of the reagent papers with the serum is brought about, which brings about a mixing of the serum and the reagents in the reagent papers 8 and 9. The reaction then takes place. It can be observed through the covering film 7.

FIG. 3.

This device again corresponds to the basic construction of FIG. 1 but, instead of the intermediate fabric 3, there is provided an optical barrier layer 10. This barrier layer 10 is permeated with barium sulphate, titanium dioxide or similar strongly reflecting substances and usually consists of a synthetic resin or gelatine film. By means of this layer 10, on the one hand, light beamed in for the observation of the reaction is completely remitted and, on the other hand, any discolorations of the zone 4 are not visible.

FIG. 4.

With regard to the serum-obtaining part, this again corresponds to FIG. 1. The reagent zone 2, which here consists of a reagent film, is, in this case, applied to one side of a multifilar fabric 11 which, on the one hand, serves to stabilise the reagent film and, on the other hand, promotes wetting by the serum and the admission of atmospheric oxygen. The fabric 11 and the loosely applied covering foil 7 are, in turn, fixed at a point of adhesion 13 on to the carrier foil 12. By pressure on the covering foil 7, there is produced contact between the serum present in the zone 4 and the reagent zone 2 and the reaction commences.

There is, of course, also the possibility of incorporating the compounds according to the present invention into gelatine matrices according to Federal Republic of Germany Patent Specification No. 2,735,690, together with the reagents and adjuvants necessary for the appropriate detection reaction.

To summarise, it can be said that the compounds of general formula I according to the present invention can be used in all test systems, with the help of which hydrogen peroxide or peroxidate-active substances can be detected directly or after preceding reactions.

The new compounds of general formula I according to the present invention can be prepared in one of the following ways:

(a) a compound of general formula:

in which $R_1$, $R_2$ and $R_3$ have the above-given meanings, is reacted with a Lewis acid or pentasulphide; or (b) when X is an oxygen atom, a compound of the general formula:

in which $R_1$, $R_2$ and $R_3$ have the above-given meanings, is reacted with ammonium acetate in glacial acetic acid; or (c) when X is a sulphur atom, a thioamide of the general formula:

in which $R_2$ has the above-given meaning, is reacted with an α-halogenoketone of the general formula:

in which $R_1$ has the above-given meaning and Hal is a fluorine, chlorine or bromine atom, and subsequently, if desired, the compound obtained is converted into another compound of general formula I and also, if desired, a base obtained is converted into a salt or a salt obtained is converted into a free base.

More particularly, the preparation of compounds of general formula I takes place as follows:

The reaction of aromatic α-acyloxyketone (prepared by the acylation of acyloins or benzoins with acid halides in pyridine or by the reaction of α-bromoketones with salts of carboxylic acids in dimethylformamide) with ammonium acetate in glacial acetic acid by Davidson's method, leads, with the introduction of imino nitrogen and ring closure, to 2,4-diaryl-substituted 1,3-oxazoles. Corresponding benzoin esters can be used for the synthesis of 2,4,5-triaryl-substituted 1,3-oxazoles.

The cyclisation of α-oximinoketones with aromatic aldehydes by the action of gaseous hydrogen chloride in glacial acetic acid gives, in the case of subsequent reduction of the resultant 1,3-oxazole-N-oxides with zinc and acetic acid, depending upon the constitution of the starting material, 2,4- or 2,5-diaryl-substituted 1,3-oxazoles. By the condensation of appropriately substituted α-acylaminoketones with polyphosphoric acid ethyl ester, 2,5-diaryl- or 2,4,5-triaryl-substituted 1,3-oxazoles (Robinson-Gabriel's method) are obtained analogously. 2,5-Diaryl-substituted 1,3-oxazoles can also be obtained from aldehyde cyanohydrins and aldehydes by condensation with ethereal hydrochloric acid (Fischer's oxazole synthesis).

The reaction of a 2-substituted 4-aminophenyl-5-methyl-1,3-oxazole with formaldehyde in methanol leads, inter alia to the formation of the N,N-bismethyl ether, the reductive methylation of the hydrochloride of this compound with formaldehyde in the presence of platinum oxide and catalytically-activated hydrogen leading to the N,N-dimethyl compound.

By alkylation of 2-substituted 4-aminophenyl-5-methyl-1,3-oxazole with 2,3-epoxypropan-1-ol or epichlorohydrin, there is obtained the corresponding aminopropandiol or the aminochloropropanol derivative, respectively.

By substitution of the halogen in the above-mentioned aminochloropropanol by reaction with morpholine, there is obtained the corresponding morpholine derivative. The reaction of the 2-substituted 4-aminophenyl-5-methyl-1,3-oxazole with diethyl 2,3-epoxypropane-phosphonate leads to diethyl 1,3-oxazolephosphonate which, by hydrolysis with 6N hydrochloric acid, can easily be converted into the phosphonic acid in question.

Reductive alkylation of the above-mentioned phosphonic acid with formaldehyde gives the N-methylated derivative, saponification of which with 6N hydrochloric acid gives the free phosphonic acid.

By the reaction of benzyl bromoacetate with a 2-substituted 4-aminophenyl-5-methyl-1,3-oxazole, there is obtained the corresponding benzyl acetate from which, by catalytic debenzylation, there is obtained the aminoacetic acid in question.

The reaction of 4-dimethylamino-α-bromoacetophenone with 4-benzyloxy-3,5-dimethoxyphenylthioamide by Hantzsch's method and subsequent hydrolytic acidic debenzylation gives the diaryl-substituted 1,3-thiazole.

From diaryl-α-acylaminoketones, there are obtained, with phosphorus pentasulphide, the corresponding 2,4,5-triaryl-substituted 1,3-thiazoles.

For ease of writing, in the following Examples, the extinctions are given as $\epsilon' = \epsilon 10^{-3}$.

Preferred compounds according to the present invention include the following:

1. 2-(3,5-dimethoxy-4-hydroxyphenyl)-4-(4-dimethylaminophenyl)-5-butyl-1,3-oxazole
2. 2-(3,5-dimethoxy-4-hydroxyphenyl)-4-(4-dimethylaminophenyl)-5-(3-propoxymethyl)-1,3-oxazole
3. 2-(3,5-dimethoxy-4-hydroxyphenyl)-4-(4-dimethylaminophenyl)-5-(4-n-butoxymethyl)-1,3-oxazole
4. 2-(3,5-dimethoxy-4-hydroxyphenyl)-4-(4-dimethylaminophenyl)-5-(tert.-butyl)-1,3-oxazole
5. 2-(3,5-dimethoxy-4-hydroxyphenyl)-4-(4-dimethylaminophenyl)-5-cyclohexyl-1,3-oxazole
6. 2-(3,5-dimethoxy-4-hydroxyphenyl)-4-(4-dimethylaminophenyl)-5-benzyl-1,3-oxazole
   2-(3,5-dimethoxy-4-hydroxyphenyl)-4-(1,2,3,4-tetrahydroquinolino-6-N-methyl)-5-methyl-1,3-oxazole
8. 2-(3,5-dimethoxy-4-hydroxyphenyl)-4-(9-julolidino)-5-methyl-1,3-oxazole
9. 2,4-bis-(3,5-dimethoxy-hydroxyphenyl)-5-methyl-1,3-oxazole
10. 2,5-bis-(3,5-dimethoxy-4-hydroxyphenyl)-4-methyl-1,3-oxazole
11. 2-(3,5-di-tert.-butyl-4-hydroxyphenyl)-4-(4-dimethylaminophenyl)-1,3-oxazole
12. 2-(3,5-di-tert.-butyl-4-hydroxyphenyl)-4-(4-dimethylaminophenyl)-5-butyl-1,3-oxazole
13. 2-(3,5-di-tert.-butyl-4-hydroxyphenyl)-4-(4-dimethylaminophenyl)-5-(3-methoxypropyl)-1,3-oxazole
14. 2-(3,5-di-tert.-butyl-4-hydroxyphenyl)-4-(4-dimethylaminophenyl)-5-(5-methoxypentyl)-1,3-oxazole
15. 2-(3,5-di-tert.-butyl-4-hydroxyphenyl)-4-(4-dimethylaminophenyl)-5-(tert.-butyl)-1,3-oxazole
16. 2-(3,5-di-tert.-butyl-4-hydroxyphenyl)-4-(4-dimethylaminophenyl)-5-cyclohexyl-1,3-oxazole
17. 2-(3,5-di-tert.-butyl-4-hydroxyphenyl)-4-(4-dimethylaminophenyl)-5-benzyl-1,3-oxazole
18. 2-(3,5-di-tert.-butyl-4-hydroxyphenyl)-4-(1,2,3,4-tetrahydroquinolino-6-N-methyl)-5-methyl-1,3-oxazole
19. 2-(3,5-di-tert.-butyl-4-hydroxyphenyl)-4-(9-julolidino)-5-methyl-1,3-oxazole
20. 2-(3,5-di-tert.-butyl-4-hydroxyphenyl)-4-methyl-5-(9-julolidino)-1,3-oxazole
21. 2-(1,2,3,4-tetrahydroquinolino-6-N-methyl)-4-(3,5-dimethoxy-4-hydroxyphenyl)-5-methyl-1,3-oxazole
22. 2-(9-julolidino)-4-(3,5-dimethoxy-4-hydroxyphenyl)-5-methyl-1,3-oxazole
23. 2,4-bis-(4-dimethylaminophenyl)-5-(3,5-dimethoxy-4-hydroxyphenyl)-1,3-oxazole
24. 2-(9-julolidino)-4,5-bis-(3,5-dimethoxy-4-hydroxyphenyl)-1,3-oxazole
25. 2-(3,5-di-tert.-butyl-4-hydroxyphenyl)-4-(4-dimethylaminophenyl)-5-phenyl-1,3-oxazole
26. 2-(3,5-di-tert.-butyl-4-hydroxyphenyl)-4,5-bis(9-julolidino)-1,3-oxazole
27. 2,4,5-tris-(3,5-di-tert.-butyl-4-hydroxyphenyl)-1,3-oxazole
28. 2-(4-dimethylaminophenyl)-4,5-bis-(3,5-di-tert.-butyl-4-hydroxyphenyl)-1,3-oxazole
29. 2-(1,2,3,4-tetrahydroquinolino-6-N-methyl)-4,5-bis-(3,5-di-tert.-butyl-4-hydroxyphenyl)-1,3-oxazole
30. 2-(9-julolidino)-4,5-bis-(3,5-di-tert.-butyl-4-hydroxyphenyl)-1,3-oxazole
31. 2-(4-dimethylaminophenyl)-4-(3,5-di-tert.-butyl-4-hydroxyphenyl)-5-methyl-1,3-oxazole
32. 2-(1,2,3,4-tetrahydroquinolino-6-N-methyl)-4-(3,5-di-tert.-butyl-4-hydroxyphenyl)-5-methyl-1,3-oxazole
33. 2-(9-julolidino)-4-(3,5-di-tert.-butyl-4-hydroxyphenyl)-5-methyl-1,3-oxazole
34. 2-(3,5-dimethoxy-4-hydroxyphenyl)-4,5-bis-(1,2,3,4-tetrahydroquinolino-6-N-methyl)-1,3-oxazole
35. 2-(3,5-dimethoxy-4-hydroxyphenyl)-4,5-bis-(9-julolidino)-1,3-oxazole
36. 2-(3,5-dimethoxy-4-hydroxyphenyl)-4-(4-dimethylaminophenyl)-5-phenyl-1,3-oxazole
37. 2-(3,5-dimethoxy-4-hydroxyphenyl)-4,5-bis-(3,5-di-tert.-butyl-4-hydroxyphenyl)-1,3-oxazole
38. 2-(1,2,3,4-tetrahydroquinolino-6-N-methyl)-4,5-bis(3,5-dimethoxy-4-hydroxyphenyl)-1,3-oxazole
39. 2-(3,5-dimethoxy-4-hydroxyphenyl)-4-4-(N-2,3-dihydroxypropyl)-aminophenyl-5-methyl-1,3-oxazole
40. 2-(3,5-dimethoxy-4-hydroxyphenyl)-4-4-(N-2,3-dihydroxypropyl)-methylaminophenyl-5-methyl-1,3-oxazole
41. N-{4-[2-(3,5-dimethoxy-4-hydroxyphenyl)-5-methyl-4-(1,3)-oxazolyl]-phenylamino}-methane-phosphonic acid
42. N-{4-[2-(3,5-dimethoxy-4-hydroxyphenyl)-5-methyl-4-(1,3)-oxazolyl]-methylphenylamino}-methane-phosphonic acid 43. N-{4-[2-(3,5-dimethoxy-4-hydroxyphenyl)-5-methyl-4-(1,3)-oxazolyl]-phenylamino}-ethanesulch-onic acid
44. N-{4-[2-(3,5-dimethoxy-4-hydroxyphenyl)-5-methyl-4-(1,3)-oxazolyl]-phenylamino}-ethanephosphonic acid
45. N-{4-[2-(3,5-dimethoxy-4-hydroxyphenyl)-5-methyl-4-(1,3)-oxazolyl]-phenylamino}-methanephosphonic acid
46. N{-4-[2-(3,5-dimethoxy-4-hydroxyphenyl)-5-methyl-4-(1,3)-oxazolyl]-methylphenylamino}-methanesulphonic acid
47. N-{4-[2-(3,5-dimethoxy-4-hydroxyphenyl)-54-methyl-(1,3)-oxazolyl]-methylphenylamino}-ethanephosphonic acid
48. N-{4-[2-(3,5-dimethoxy-4-hydroxyphenyl)-54-methyl-(1,3)-oxazolyl]-phenylamino}-acetic acid
49. N,N-{4-[2-(3,5-dimethoxy-4-hydroxyphenyl)-54-methyl-(1,3)-oxazolyl]-phenylamino}-bis-ethanesulphonic acid
50. N-{4-[2-(3,5-dimethoxy-4-hydroxyphenyl)-5-methyl-4-(1,3)-oxazolyl]-phenylamino}-bis-methanephosphonic acid
51. N,N-{4-[2-(3,5-dimethoxy-4-hydroxyphenyl)-5-methyl-4-(1,3)-oxazolyl]-phenylamino}-bis-acetic acid
52. {4-[2-(3,5-dimethoxy-4-hydroxyphenyl)-5-methyl-4-(1,3)-oxazolyl-]1,2,3,4-tetrahydroquinolino}-6-N-ethanesulfonic acid
53. {2-[4-(3,5-dimethoxy-4-hydroxyphenyl)-5-methyl-4-(1,3)-oxazolyl-]1,2,3,4-tetrahydroquinolino}-6-N-ethanesulfonic acid
54. {4-[2-(3,5-dimethoxy-4-hydroxyphenyl)-5-methyl-4-(1,3)-oxazolyl]-1,2,3,4-tetrahydroquinolino}-6-N-ethanephosphonic acid
55. {2-[4-(3,5-dimethoxy-4-hydroxyphenyl)-5-methyl-4-(1,3)-oxazolyl]-1,2,3,4-tetrahydroquinolino}-6-N-ethanephosphonic acid
56. {4-[2-(3,5-dimethoxy-4-hydroxyphenyl)-5-methyl-4-(1,3)-oxazolyl]-1,2,3,4-tetrahydroquinolino}-6-N-acetic acid
57. {2-[4-(3,5-dimethoxy-4-hydroxyphenyl)-5-methyl-4-(1,3)-oxazolyl]-1,2,3,4-tetrahydroquinolino}-6-N-acetic acid
58. 2-(3,5-dimethoxy-4-hydroxyphenyl)-4-(4-dimethylaminophenyl)-5-hydroxymethyl-1,3-oxazole
59. {5-[2-(3,5-dimethoxy-4-hydroxyphenyl)-4-(4-dimethylaminophenyl)-(1,3)-oxazolyl]-methyl}-trimethylammonium chloride
60. -{5-[2-(3,5-dimethoxy-4-hydroxyphenyl)-4-(4-dimethylaminophenyl)-(1,3)-oxazolyl]-methyl}pyridinium chloride
61. 2-(3,5-di-tert.-butyl-4-hydroxyphenyl)-4-(4-N-3-chloro-2-hydroxypropylaminophenyl)-5-methyl-1,3-oxazole
62. 2-(3,5-di-tert.-butyl-4-hydroxyphenyl)-4-[4-(N-2,3-dihydroxypropyl)-aminophenyl]-5-methyl-1,3-oxazole
63. 2-(3,5-di-tert.-butyl-4-hydroxyphenyl)-4-[4-(N-2,3-dihydroxypropyl)-methylaminophenyl]-5-methyl-1,3-oxazole
64. N-{4-[2-(3,5-di-tert.-butyl-4-hydroxyphenyl)-5-methyl-4-(1,3)-oxazolyl]-phenylamino}-methanephosphonic acid
65. N-{4-[2-(3,5-di-tert.-butyl-4-hydroxyphenyl)-5-methyl-4-(1,3)-oxazolyl]-methylphenylamino}-methanephosphonic acid
66. 2-(3,5-di-tert.-butyl-4-hydroxyphenyl)-4-[4-(3-N-morpholino-2-hydroxypropyl)-aminophenyl-]5-methyl-1,3-oxazole
67. diethyl N-{4-[2-(3,5-di-tert.-butyl-4-hydroxyphenyl)-5-methyl-4-(1,3)-oxazolyl]-phenylamino-2-hydroxypropyl}-phosphonate
68. N-{4-[2-(3,5-di-tert.-butyl-4-hydroxyphenyl)-5-methyl-4-(1,3)-oxazolyl]-phenylamino-2-hydroxypropyl}-phosphonic acid
69. N-{4-[2-(3,5-di-tert.-butyl-4-hydroxyphenyl)-5-methyl-4-(1,3)-oxazolyl]-methylphenylamino-2-hydroxypropyl}-phosphonic acid
70. N-{4-[2-(3,5-di-tert.-butyl-4-hydroxyphenyl)-5-methyl-4-(1,3)-oxazolyl]-phenylamino}-ethanesulphonic acid
71. N-{4-[2-(3,5-di-tert.-butyl-4-hydroxyphenyl)-5-methyl-4-(1,3)-oxazolyl]-phenylamino}-ethanephosphonic acid
72. N-{4-[2-(3,5-di-tert.-butyl-4-hydroxyphenyl)-5-methyl-4-(1,3)-oxazolyl]-phenylamino}-methanephosphonic acid
73. N-{4-[2-(3,5-di-tert.-butyl-4-hydroxyphenyl)-5-methyl-4-(1,3)-oxazolyl]-methylphenylamino}-methanesulphonic acid
74. N-{4-[2-(3,5-di-tert.-butyl-4-hydroxyphenyl)-5-methyl-4-(1,3)-oxazolyl]-methylphenylamino}-ethanephosphonic acid
75. N,N-{4-[2-(3,5-di-tert.-butyl-4-hydroxyphenyl)-5-methyl-4-(1,3)-oxazolyl]-phenylamino}-bis-ethanesulphonic acid
76. N,N-{4-[2-(3,5-di-tert.-butyl-4-hydroxyphenyl)-5-methyl-4-(1,3)-oxazolyl]-phenylamino}-bis-methanephosphonic acid
77. N,N-{4-[2-(3,5-di-tert.-butyl-4-hydroxyphenyl)-5-methyl-4-(1,3)-oxazolyl]-phenylamino}-bis-acetic acid
78. {4-[2-(3,5-di-tert.-butyl-4-hydroxyphenyl)-5-methyl-4-(1,3)-oxazolyl]-1,2,3,4-tetrahydroquinolino-6-N-ethanesulphonic acid
79. {2-[4-(3,5-di-tert.-butyl-4-hydroxyphenyl)-5-methyl-4-(1,3)-oxazolyl]-1,2,3,4-tetrahydroquinolino-}6-N-ethanesulphonic acid
80. {4-[2-(3,5-di-tert.-butyl-4-hydroxyphenyl)-5-methyl-4-(1,3)-oxazolyl]-1,2,3,4-tetrahydroquinolino}-6-N-ethanephosphonic acid
81. {2-[4-(3,5-di-tert.-butyl-4-hydroxyphenyl)-5-methyl-4-(1,3)-oxazolyl]-1,2,3,4-tetrahydroquinolino}-6-N-ethanephosphonic acid
82. {4-[2-(3,5-di-tert.-butyl-4-hydroxyphenyl)-5-methyl-4-(1,3)-oxazolyl]-1,2,3,4-tetrahydroquinolino-}6-N-acetic acid
83. {2-[4-(3,5-di-tert.-butyl-4-hydroxyphenyl)-5-methyl-(1,3)-oxazolyl]-1,2,3,4-tetrahydroquinolino}-6-N-acetic acid
84. 2-(3,5-di-tert.-butyl-4-hydroxyphenyl)-4-(4-dimethylaminophenyl)-5-hydroxymethyl-1,3-oxazole
85. {5-[2-(3,5-di-tert.-butyl-4-hydroxyphenyl)-4-(4-dimethylaminophenyl)-(1,3)-oxazolyl]-methyl}-trimethylammonium chloride
86. 1-{5-[2-(3,5-di-tert.-butyl-4-hydroxyphenyl)-4-(4-dimethylaminophenyl)-(1,3)-oxazolyl]-methyl} pyridinium chloride
87. {5-[4-(4-dimethylaminophenyl)-5-methyl-2-(1,3)]-oxazolyl]-2-hydroxy-3-methoxy}-phenyloxyacetic acid
88. {5-[4-(4-dimethylaminophenyl)-5-methyl-2-(1,3)-oxazolyl-2-hydroxy-3-tert.-butyl}-phenoxyacetic acid 89. {5-[2-(4-dimethylaminophenyl)-5-methyl-4-(1,3)-oxazolyl]-2-hydroxy-3-methoxy}-phenoxyacetic acid 90. {5-[2-(4-dimethylaminophenyl)-5-methyl-4-(1,3)-oxazolyl]-2-hydroxy-3-tert.-butyl}-phenoxyacetic acid 91. 2-(3,5-di-tert.-butyl-4-hydroxyphenyl)-4,5-bis-(1,2,3,4-tetrahydroquinolino-6-N-methyl)-1,3-oxazole.

The following Examples are given for the purpose of illustrating the present invention:

EXAMPLE 1

2-(3,5-Dimethoxy-4-hydroxyphenyl)-4-(4-dimethylaminophenyl)-1,3-oxazole hydrochloride (a) 4-N,N-Dimethylamino-α-[(3,5-dimethoxy-4-hydroxy)-benzyloxy]-acetophenone.

A suspension of 48 g. (0.2 mol) 4-dimethylamino-α-bromoacetophenone and 48.4 g. (0.22 mol) sodium syringate in 1.2 liters of anhydrous dimethylformamide is heated for 2 hours at 130° C., while stirring. After evaporating the solvent in a vacuum to about one third of its volume, 1 liter of ice water is added thereto, the crystals formed are filtered off with suction, the filter cake is washed with 500 ml. water and the crude product is recrystallised from 400 ml. acetic acid. After suction filtration, the crystals are washed with 200 ml. water and 200 ml acetone. Subsequently, the product is dried in a vacuum at 40° C. to give 42.1 g. (55% of theory) of the title compound in the form of beige-coloured crystals; m.p. 208°–210° C. (b) 36 g. (0.1 mol) of the ester obtained in (a) above are heated in 500 ml. glacial acetic acid with 38.6 g. (0.5 mol) ammonium acetate for 2 hours at 130° C. while stirring. After cooling, the reaction mixture is poured into 2 liters of ice water and the crystals are filtered off with suction and washed with water and diethyl ether to give 15.1 g. of beige-coloured crystals. The crude product is purified column chromatographically on silica gel with chloroform-methanol (9:1 v/v). The appropriate fraction gives, upon evaporation, 7.3 g. (20.6% of theory) of the title compound; m.p. 202°–204° C. (decomp ); $\lambda_{max}$=498 nm, $\epsilon'$=20.5 cm$^2$ μmol$^{-1}$.

The following compounds are obtained analogously:

1.1. 2,4-Bis-(3,5-dimethoxy-4-hydroxyphenyl)-1,3-oxazole (a) 3,5-Dimethoxy-4-hydroxy-α-[(3,5-dimethoxy-4-hydroxy)-benzyloxy]-acetophenone; yield 94% of theory: m.p. 147°/153° C.

(b) Title compound (base); yield 29% of theory; m.p. 168°–172° C. Hydrochloride; m.p. 132°–134° C. (decomp.); $\lambda_{max}$ 470 nm; $\epsilon'$ =14.4 cm$^2$ μmol$^{-1}$.

1.2. 2-(4-Dimethylaminophenyl)-4-(3,5-dimethoxy-4-hydroxyphenyl)-1,3-oxazole hydrochloride (a) 4-Benzyloxy-3,5-dimethoxy-α-(4-dimethylaminobenzoyloxy)-acetophenone; yield 53% of theory; m.p. 114° C.

(b) 2-(4-Dimethylaminophenyl)-4-(4-benzyloxy-3,5-dimethoxyphenyl)-1,3-oxazole; yield 16% of theory; m.p. 157° C.

(c) 4.3 g. (0.01 mol) of the oxazole derivative obtained in (b) are hydrogenated in 100 ml. ethanol, by the addition of 0.3 g. 10% palladium on active charcoal, at 25° C. under normal pressure. After filtering off the catalyst and evaporating the filtrate, there are obtained 2.7 g. of the title compound; yield 65% of theory; m.p. 185° C.; $\lambda_{max}$=512 nm, $\epsilon'$=5.3 cm$^2$ μmol$^{-1}$.

1.3. 2-(4-Dimethylaminophenyl)-4-(3,5-dimethoxy-4-hydroxyphenyl)-5-methyl-1,3-oxazole hydrochloride (a) 3,5-Dimethoxy-4-hydroxy-α-(4-dimethylaminobenzoyloxy)propiophenone; yield 40.5% of theory; m.p. 152°–155° C. (decomp.).

(b) Title compound; yield 20.5% of theory: m.p. 128° C.; $\lambda_{max}$ 327 nm, $\epsilon'$=78.9 cm$^2$ μmol$^{-1}$.

1.4. 2-(9-Julolidino)-4-(3,5-dimethoxy-4-hydroxyphenyl)-1,3-oxazole hydrochloride (a) 3,3-Dimethoxy-4-hydroxy-α-(9-julolidinocarboxy)acetophenone, purification by chromatography on silica gel, elution agent: chloroform; yield 42.8% of theory, amorphous powder TLC: silica gel plate, elution agent: n-heptanemethyl ethyl ketone (1:1 v/v). RF value: 0.48

(b) Title compound; yield 25.6% of theory; colourless crystals; m.p. 231°–233° C. $\lambda_{max}$ 540 nm, $\epsilon''$=21.6 cm$^2$ μmol$^{-1}$.

1.5. 2-(3,5-Di-tert.-butyl-4-hydroxyphenyl)-4-(4dimethylaminophenyl)-5-methyl-1,3-oxazole (a) 4-Dimethylamino-α-[(3,5-di-tert.-butyl-4-hydroxy)benzoyloxy] -propiophenone; yield 85.6% of theory; m.p. 172° C.

(b) Title compound yield 95% of theory; m.p. 125° C. (decomp.). $\lambda_{max}$ 488 nm, $\epsilon'$=46.4 cm$^2$ μmol$^{-1}$.

1.6. 2-(3,4-Di-tert.-butyl-4-hydroxyphenyl)-4-(3,5-dimethoxy-4-hydroxyphenyl)-5-methyl-1,3-oxazole (a) 4-(3,5-Dimethoxy-4-hydroxyphenyl)-α-(3,5-di-tert.-butyl-4-hydroxybenzyloxy)-propiophenone; yield 90.5% of theory; amorphous yellowish powder. TLC silica gel plate, elution agent: toluene-ethyl acetate (5:1 v/v); RF value=0.425.

(b) Title compound: yield 82.4% of theory; m.p. 83°–85° C. $\lambda_{max}$=486 nm; $\epsilon'$=31.1 cm$^2$ μmol$^1$.

1.7. 2-(3,5-Dimethoxy-4-hydroxyphenyl)-4-(4-dimethylaminophenyl)-5-phenyl-1,3-oxazole (a) 4-Dimethylamino-0-(4-benzyloxy-3,5-dimethoxybenzoyl)benzoin; m.p. 126°–128° C.

(b) 2-(3,5-Dimethoxy-4-benzyloxyphenyl)-4-(4-dimethylaminophenyl)-5-phenyl-1,3-oxazole (worked up directly).

(c) Instead of the catalytic debenzylation mentioned in Example 1.2.c), the 0-benzyl protective group is here split off, after ring closure of (a) to give the 1,3-oxazole (b), by boiling with 6N hydrochloric acid for 30 minutes to give the title compound; yield 40% of theory; m.p. 167° C. (decomp ); $\lambda_{max}$ 582 nm, $\epsilon'$=36.4 cm$^2$ μmol$^{-1}$.

1.8. 2-(3,5-Di-tert.-butyl-4-hydroxyphenyl)-4-(9-julolidino)-5-methyl-1,3-oxazole (a) 9-Julolidino-α-bromomethyl ketone From julolidine aldehyde, there is obtained, by a Grignard reaction with ethyl magnesium bromide, the corresponding carbonol; m.p. 74°–77° C. An Oppenauer oxidation of this product gives 9-julolidinoethyl ketone (m.p. 68.5°–69.5° C.) from which, by bromination in glacial acetic acid, there is obtained 9-julolidino-α-bromoethyl ketone; m.p. 82°–84° C.

(b) 9-Julolidino-α-(3,5-di-tert.-butyl-4-hydroxybenzoyloxy)-ethyl ketone; m.p. 165°–170° C.

(c) Title compound: yield 34% of theory; m.p. 135° C. (decomp.). $\lambda_{max}$=490 nm, $\epsilon'$=35.2 cm$^2$ μmol$^{-1}$.

EXAMPLE 2

2,4,5-Tris-(3,5-dimethoxy-4-hydroxyphenyl)-1,3-oxazole (a) 3,3',5,5'-tetramethoxy-4,4'-dibenzyloxybenzoin.

81.7 g. (0.3 mol) 4-Benzyloxy-3,5-dimethoxybenzaldehyde are suspended in 300 ml. ethanol, 6 g. potassium cyanide are added thereto and the reaction mixture is heated under reflux for 3 hours, the aldehyde thereby going into solution. The reaction mixture is then poured into 1.5 liters ice water and stirred for 2 hours, while cooling with ice. The crude product obtained is taken up with 2×300 ml. dichloromethane, dried with anhydrous sodium sulphate and evaporated in a vacuum. The residue, 87.3 g. of oily material, is purified by chromatography on silica gel. The appropriate fraction is evaporated to give 52.4 g of yellowish crystals of the title compound; yield 63.2% of theory; m.p. 149°–150° C.

(b) 3,3′,5,5′-tetramethoxy-4,4′-dibenzyloxy-0-(4-benzoyloxy-3,5-dimethoxybenzoyl)-benzoin 15.8 g. (0.029 mol) of the above-mentioned benzoin derivative are suspended in 40 ml. pyridine and, while stirring, a solution of 13.4 g. (0.0435 mol) 4-benzyloxy-3,5-dimethoxybenzoyl chloride in 80 ml. anhydrous pyridine is added dropwise thereto. After 8 hours at ambient temperature, the reaction mixture is evaporated in a vacuum on a rotary evaporator, the residue is taken up in 100 ml. dichloromethane, the solution is successively shaken with 2N hydrochloric acid, water, 2N aqueous sodium carbonate solution and water and then evaporated in a vacuum. There are obtained 25 g. of the oily title compound. TLC: silica gel 60, elution agent: isopropanol/n-butyl acetate/water/ammonia (5:2:1.5:0.5 v/v/v/v).

(c) 2,4,5-Tris-(4-benzyloxy-3,5-dimethoxyphenyl)-1,3-oxazole 20 g. (0.0245 mol) of the compound obtained under (b) are heated with 28.4 g. (0.37 mol) ammonium acetate in 250 ml. glacial acetic acid for 5 hours under reflux, thereafter the reaction mixture is poured into a mixture of 500 ml. water and 250 ml. concentrated ammonia and the precipitated crystalline crude product is filtered off, washed with water and dried. Yield 24.6 g. For purification, the product is chromatographed on silica gel; elution agent: toluene-ethyl acetate (4:1 v/v). There are obtained 13 g. (yield 66.4% of theory) of beige-coloured crystals of the title compound; m.p. >80° to 120° C. (no sharp melting point). TLC: silica gel, elution agent: toluene-ethyl acetate (4:1 v/v); RF value=0.64.

(d) 11 g. (0.014 mol) of the above oxazole are dissolved in 300 ml. methanol and, after the addition of 1.1 g. palladium on charcoal (10%), hydrogenated at normal pressure. After the take up of the calculated amount of hydrogen, the catalyst is filtered off and the filtrate is mixed with 7.5 ml. 5N ethereal hydrochloric acid and evaporated in a vacuum. There are obtained 7 g. (yield 82.1% of theory) of the title compound in the form of colourless crystals; m.p. 205°–207° C. (decomp.); $\lambda_{max}$ 632 nm, $\epsilon'=22.2$ cm$^2$ $\mu$mol$^{-1}$.

The following compound is obtained in an analogous way:

2.1. 2-(3,5-Di-tert.-butyl-4-hydroxyphenyl)-4,5-bis-(3,5-dimethoxy-4-hydroxyphenyl)-1,3-oxazole (a) 3,3′,5,5′-Tetramethoxy-4,4′-dibenzyloxy-α-(4-hydroxy-3,5-di-tert.-butyl)-benzoyloxybenzoin
Yield: 42.5% of theory; yellowish amorphous powder. TLC silica gel 60, elution agent: toluene-ethyl acetate (5:1 v/v); RF value=0.61.

(b) 2-(3,5-Di-tert.-butyl-4-hydroxyphenyl)-4,5-bis-(3,5-dimethoxy-4-benzyloxyphenyl)-1,3-oxazole.
Yield: 62.5% of theory; reddish oil TLC: silica gel 60; elution agent: toluene-ethyl acetate (5:1 v/v): RF value=0.56.

(c) Title compound: yield 81.5% of theory; m.p. 120° C. (decomp.); $\lambda_{max}$ 587 nm, $\epsilon'=40.2$ cm$^2$ $\mu$mol$^{-1}$.

EXAMPLE 3

2-(3,5-Dimethoxy-4-hydroxyphenyl)-4-(4-aminophenyl)-5-methyl-1,3-oxazole hydrochloride (a) 2-(3,5-Dimethoxy-4-hydroxyphenyl)-4-acetaminophenyl-5-methyl-1,3-oxazole N-oxide.

50 g. (0.227 mol) 4-acetaminophenyl-1-oximino-2-propanone and 41.35 g. (0.227 mol) 3,5-dimethoxy-4-hydroxybenzaldehyde are suspended in 600 ml. glacial acetic acid and, while stirring, dry hydrogen chloride gas is passed through the reaction mixture for 5 hours, whereafter the reaction mixture is evaporated to one half in a vacuum. After the addition of 200 ml. ethanol, the mixture is filtered and the filter cake is washed with 150 ml. ethanol. Yield 75.6 g. (80% of theory) of the title compound; brownish crystals; m.p. >200° C. (decomp.). TLC: silica gel; elution agent: chloroform-methanol (8:1 v/v); RF value=0.31.

(b) 75.62 g. (0.182 mol) of the above-mentioned product are suspended in 900 ml. glacial acetic acid and, while stirring, 220 g. (3.35 g. atom) zinc dust are added thereto portionwise. Thereafter, the reaction mixture is heated under reflux for 2 hours, filtered while hot and the filtrate evaporated in a vacuum and boiled under reflux for 30 minutes with 500 ml. 6N hydrochloric acid. The reaction mixture is cooled with ice and the crystals formed are filtered off with suction and the filter residue is washed with 150 ml. acetone. The zinc-containing crude product is dissolved in 1.2 liters hot water, mixed with a solution of 55 g. Titriplex III in 1.5 liters water and the base liberated by the addition of 50 ml. concentrated aqueous ammonia solution. After filtering off and washing the filter residue with water, it is recrystallised from 6N hydrochloric acid and, after filtering off, washing the hydrochloride with acetone and drying in a vacuum at 40° C., there are obtained 60.2 g. (79.8% of theory) of the title compound; m.p. 253°–255° C. (decomp.); $\lambda_{max}$ 540 nm, $\epsilon'=29$ cm$^2$ $\mu$mol$^{-1}$.

The following compounds are obtained in an analogous manner:

3.1. 2-(3,5-dimethoxy-4-hydroxyphenyl)-4-(4-amino-3-methoxyphenyl)-5-methyl-1,3-oxazole hydrochloride from 4-acetamino-3-methoxyphenyl-1-oximino-2-propanone and 3,5-dimethoxy-4-hydroxybenzaldehyde; m.p. >227° C. (decomp.); yellowish crystals; $\lambda_{max}$ 546 nm, $\epsilon'=21.6$ cm$^2$ $\eta$mol$^{-1}$.

3.2. 2-(3,5-dimethoxy-4-hydroxyphenyl)-4-methyl-5-(4-dimethylaminophenyl)-1,3-oxazole hydrochloride from 4-dimethylaminophenyl-2-oximino-1-propanone and 3,5-dimethoxy-4-hydroxybenzaldehyde; m.p. 168°–170° C. (decomp.); colourless crystals; $\lambda_{max}$ 494 nm, $\epsilon'=5.7$ cm$^2$ $\mu$mol$^{-1}$.

3.3. 2-(3,5-di-tert.-butyl-4-hydroxyphenyl)-4-(4-aminophenyl)-5-methyl-1,3-oxazole hydrochloride from 4-acetaminophenyl-1-oximino-2-propanone and 3,5-di-tert.-butyl-4-hydroxybenzaldehyde via the oxime; (oxime m.p. 215° C. (decomp.)); colourless crystals; m.p. 238° C.; TLC: silica gel 60, elution agent: chloroform-methanol (19:1 v/v); RF value: 0.65 (base); $\lambda_{max}$ 514 nm; $\epsilon'=41.6$ cm$^2$ $\mu$mol$^{-l}$.

3.4. 2-(4-Dimethylaminophenyl)-bis-4,5-(3,5-dimethoxy-4-hydroxyphenyl)-1,3-oxazole hydrochloride.

(a) Bis-(3,3′,5,5′)-tetramethoxy-4,4′-benzyloxybenzil monoxime 27.13 g. (0.05 mol) bis-(3,3′,5,5′-tetramethoxy-4,4′-benzyloxybenzil are suspended in 350 ml. dry pyridine, 6.35 g. (0.1 mol) hydroxylamine hydrochloride are added thereto and the reaction mixture is stirred for 4.5 hours at ambient temperature, thereafter evaporated in a vacuum and the residue is separated chromatographically on the silica gel column; elution agent: toluene-ethyl acetate (2:1 v/v). The appropriate fraction contains 17.3 g. (62% of theory) of oxime; reddish oil. TLC: silica gel 60; elution agent: toluene-ethyl acetate (2:1 v/v); RF value=0.64.

(b) 14.49 g. (0.026 mol) of the above compound are dissolved in 50 ml. glacial acetic acid, together with 3.88 g. (0.026 mol) 4-dimethylaminobenzaldehyde, and dry hydrogen chloride is passed in at 15° to 20° C., while stirring, for 3.5 hours. Thereafter, the reaction mixture is substantially evaporated in a vacuum, the residue is stirred with diethyl ether and the crude product obtained is purified on silica gel; elution agent: dichloromethane-acetone-methanol (20:10:2 v/v/v). There are obtained 3.1 g. (21.1% of theory) of beige-coloured crystals: m.p. 212°–215° C. (decomp.); $\lambda_{max}$ 619 nm, $\epsilon'=25.9$ cm$^2$ $\mu$mol$^{-1}$.

EXAMPLE 4

2-(3,5-Dimethoxy-4-hydroxyphenyl)-4,5-bis-(4-dimethylaminophenyl)-1,3-oxazole (a) 4,4′-Bis-(dimethylamino)-benzil monoxime.

74 g. (0.25 mol) 4,4′-bis-(dimethylamino)-benzil are stirred with 20.8 g. (0.3 mol) hydroxylamine hydrochloride in 1.2 liters pyridine for 30 hours at ambient temperature. The reaction mixture is then evaporated to dryness in a vacuum, stirred with 500 ml. water, subsequently with 500 ml. of a mixture of methanol and water (1:3 v/v) and finally with 500 ml. toluene, filtered off with suction and dried. There are obtained 69.6 g. (89.2% of theory) 4,4′-bis-(dimethylamino)-benzil monoxime; m.p. 179° C. (decomp ). (b) 4,4′-Bis-(dimethylamino)-2-aminodesoxybenzoin hydrochloride 10 g. (0.032 mol) of the compound obtained in (a) are hydrogenated in 60 ml. 6N methanolic hydrochloric acid at ambient temperature in the presence of 1.93 g. palladium on charcoal. After ending of the take up of hydrogen, the catalyst is filtered off with suction and the filtrate is evaporated in a vacuum. After recrystallisation of the residue from methanol, there are obtained 9.1 g. (84% of theory) of yellowish crystals of the title compound: m.p. 218°–220° C. (decomp.).

(c) 4,4′-Bis-(dimethylamino)-2-(4-benzyloxy-3,5-dimethoxybenzamino)-desoxybenzoin.

33.64 g. (0.11 mol) 4-benzyloxy-3,5-dimethoxybenzoyl chloride are dissolved in 250 ml. anhydrous pyridine, then a suspension of 33.4 g. (0.1 mol) of the compound obtained under (b) in 300 ml. anhydrous pyridine is added thereto dropwise at 5° to 10° C. and the reaction mixture is stirred for 8 hours at 40° C. and evaporated in a vacuum. The residue is taken up in 200 ml. dichloromethane, shaken up three times in each case with 100 ml. 2N hydrochloric acid, 100 ml. water, 100 ml. aqueous sodium bicarbonate solution and 100 ml. water, dried over anhydrous sodium sulphate and evaporated. The crude product, 53.2 g. of semicrystalline material, is dissolved hot in a mixture of 650 ml. toluene-methanol (12:1 v/v) and the oily product obtained is brought to crystallisation by trituration with diethyl ether. There are obtained 33.1 g. (58.3% of theory) of beige-coloured crystals; m.p. 207° C. (decomp.) of the title compound.

(d) 2-(3,5-Dimethoxy-4-benzyloxyphenyl)-4,5-bis-[4-(dimethylaminophenyl]-1,3-oxazole.

28.3 g. (0.05 mol) of the above-mentioned compound are heated under reflux for 7 hours with 243 g. (0.75 mol) polyphosphoric acid ethyl ester in 300 ml. anhydrous chloroform, thereafter neutralised by the addition of 6N ammonia solution and the reaction product is extracted with dichloromethane and the organic phase is shaken up with water, dried over anhydrous sodium sulphate and evaporated. The title compound, 30 g. of brown oil, is used directly, without purification, for the next step. TLC: silica gel 60; elution agent: chloroform-ethyl acetate (4:1 v/v); RF value=0.66. (e) 28 g. (0.05 mol) of the crude product obtained according to (d) are boiled under reflux for 1 hour with 200 ml. 6N hydrochloric acid. Thereafter, the reaction mixture is evaporated in a vacuum and the residue is recrystallised twice from methanol-acetone (2:1 v/v). The pale yellow title compound is filtered off and the filter cake is washed with acetone and dried in a vacuum at 50° C. Yield 16.1 g. (35.1% of theory) of colourless crystals; m.p. 232°–234° C. (decomp.); $\lambda_{max}$ 550 nm, $\epsilon'=8.57$ cm$^2$ $\mu$mol$^{-1}$.

4.1. 2-(3,5-Dimethoxy-4-hydroxyphenyl)-5-(4-dimethylaminophenyl)-1,3-oxazole hydrochloride.

(a) 4-Dimethylamino-ω-aminoacetophenone hydrochloride.

6 g. (0.03 mol) 4-Dimethylamino-ω-hexamethylenetetraminium· acetophenone bromide are suspended in 28 ml. ethanol and, after the addition of 14 ml. concentrated hydrochloric acid, stirred for 3 days at ambient temperature, thereafter filtered off and the filtrate evaporated in a vacuum. There are obtained 5 g. 4-dimethylamino-ω-aminoacetophenone hydrochloride; m.p. 185° C. (decomp.).

(b) 4-Dimethylamino-ω-(4-benzyloxy-3,5-dimethoxybenzamido)-acetophenone.

4.81 g. of the above compound from (a) are suspended in 50 ml. anhydrous pyridine and a solution of 7.56 g. (0.025 mol) 4-benzyloxy-3,5-dimethoxybenzoyl chloride in 70 ml. anhydrous pyridine is added dropwise thereto, while cooling with ice. After 6 hours, the reaction mixture is filtered and the filtrate evaporated in a vacuum. After taking up the residue in dichloromethane, it is shaken up with water and 2N hydrochloric acid, the organic phase is dried and evaporated in a vacuum and the residue is triturated with 50 ml. diethyl ether. There are obtained 7.11 g of the title compound; m.p. 128°–131° C. (decomp.). (c) 5 g. (0.01 mol) of the compound from (b) are heated under reflux with 54.4 g. (0.16 mol) polyphosphoric acid ethyl ester in 300 ml. anhydrous chloroform for 5 hours under an atmosphere of argon. Subsequently, the reaction mixture is evaporated on a rotary evaporator. There is obtained a light brownish oil which is boiled under reflux with 150 ml 6N hydrochloric acid for 20 minutes, evaporated in a vacuum and purified chromatographically on a silica gel column, first with heptane-acetone (1:1 v/v) and then with methanol-acetone (1:1 v/v). There are obtained 2.6 g. of amorphous, beige-coloured compound. TLC silica gel plate: elution agent: chloroform-methyl ethyl ketone-methanol-glacial acetic acid-water (7.5/2.5/3.5/0.5/0.9 v/v/v/v/v); $\lambda_{max}$ 353 nm, $\epsilon'=8.7$ cm$^2$ $\mu$mol$^{-1}$.

EXAMPLE 5

2,5-Bis-(3,5-dimethoxy-4-hydroxyphenyl)-1,3-oxazole (a) 3,5-Dimethoxy-4-hydroxybenzaldehyde cyanhydrin.

10 g. (0.055 mol) 3,5-Dimethoxy-4-hydroxybenzaldehyde are warmed, while stirring with 10 g. (0.1 mol) sodium hydrogen sulphite in 100 ml. water, dissolving thereby taking place. Thereafter, while stirring, 2.7 g. (0.055 mol) sodium cyanide in 13 ml. water are added dropwise thereto within the course of 30 minutes, stirring is continued for 30 minutes and the cyanhydrin formed is then extracted by shaking out three times with 50 ml. amounts of diethyl ether. After drying the ethereal phase over anhydrous sodium sulphate, the solution is used directly in step (b). TLC silica gel; elution agent: chloroform-methanol (5:1 v/v), RF value=0.88; elution agent chloroform-tetrahydrofuran (1:1 v/v), RF value=0.8. ((b) The ethereal solution from 5(a) is mixed with 2.2 g. (0.014 mol) 3,5-dimethoxy-4-hydroxybenzaldehyde and, while cooling, hydrogen chloride is passed through until the solution is saturated. Upon standing, 1.06 g. (25% of theory) of the title compound crystallises out, which is obtained in pure form by taking up in water and shaking out with dichloromethane. The colourless crystals melt at 260° C. (decomp.). $\lambda_{max}$ 586 nm, $\epsilon'=29.2$ cm$^2$ µmol$^{-1}$.

EXAMPLE 6

2-(3,5-Dimethoxy-4-hydroxyphenyl)-4-(N,N-bis-methoxymethylaminophenyl)-5-methyl-1,3-oxazole 5 g. (0.0153 mol) of the compound of Example 3 (free base) are dissolved in 300 ml. methanol, 20 ml. 27% formaldehyde solution are added thereto, the reaction mixture is left to stand for 16 hours at ambient temperature and then evaporated. The residue is triturated with 200 ml. diethyl ether. There are obtained 3 g. (60.2% of theory) of pale grey, amorphous title compound. TLC silica gel; elution agent: chloroform-methanol (19:1 v/v). RF value=0.58; $\lambda_{max}$ 536 nm, $\epsilon'=33.5$ cm$^2$ mol$^{-1}$.

EXAMPLE 7

2-(3,5-Dimethoxy-4-hydroxyphenyl)-4-(4-dimethylaminophenyl)-5-methyl-1,3-oxazole hydrochloride 3.2 g. (0.0084 mol) of the compound of Example 3 (free base) are dissolved in 110 ml. methanol-water (10:1 v/v), 1.9 ml. 37% formaldehyde solution, 1 ml. concentrated hydrochloric acid, as well as 0.5 g. platinum oxide, are added thereto and hydrogenation is carried out for 4 hours to 5° to 8° C. under normal pressure. After filtering off the catalyst, the filtrate is concentrated to 50 ml. and, upon cooling, with ice, there are obtained 2 g. (51% of theory) of colourless crystals of the title compound; m.p. 250° C. (decomp.); $\lambda_{max}$ 510 nm, $\epsilon'=30$ cm$^2$ µmol$^{-1}$.

7.1. 2-(3,5-Dimethoxy-4-hydroxyphenyl)-4-(3-methoxy-4-dimethylaminophenyl)-5-methyl-1,3-oxazole hydrochloride.

In a manner analogous to that described in Example 7, from the hydrochloride of the base of Example 3.1, there is obtained, with formaldehyde solution and platinum oxide as catalyst, a yield of 82% of theory of the title compound in the form of colourless crystals; m.p. 230°–235° C. (decomp.); $\lambda_{max}$ 499 nm, $\epsilon'=29.2$ cm$^2$ µmol$^{-1}$.

EXAMPLE 8

2-(3,5-Dimethoxy-4-hydroxyphenyl)-4[-4-(2,3-dihydroxypropyl)-aminophenyl]-5-methyl-1,3-oxazole 15.9 g. (0.049 mol) of the compound of Example 3 (free base) are suspended in 320 ml. ethanol and, after the addition of 19.1 ml. (0.29 mol) 2,3-epoxypropanol, boiled under reflux for 5 hours, thereafter evaporated in a vacuum and the crude product is purified by chromatography on silica gel. Elution agent: chloroform-methanol (12:1 v/v). The appropriate fraction gives 3.32 g. (26.5% of theory) of the pale pink-coloured title compound; m.p. 165°–167° C. (decomp.); $\lambda_{max}$ 491, $\epsilon'=21.6$ cm$^2$ µmol$^{-2}$.

8.1. 2-(3,5-Dimethoxy-4-hydroxyphenyl)-4-[4-bis-(2,3-dihydroxypropyl)-aminophenyl-]5-methyl-1,3-oxazole By the reaction of 3.8 g. (0.01 mol) 2-(3,5-dimethoxy-4-hydroxyphenyl)-4-(4-aminophenyl)-5-methyloxazole with 1.41 ml. (0.029 mol) 2,3-epoxypropanol by boiling under reflux for 5 hours, there is obtained, besides the mono- compound of Example 8, also the desired bis-compound. Purification takes place by column chromatography on silica gel 60 (column 4.5 cm. diameter, filling height 70 cm.; elution agent: methylene chloride-methanol (8:1 v/v). The appropriate fractions give 2.1 g. (40% of theory) of the title compound in the form of colourless crystals; m.p. 187°–189° C. (decomp.). TLC finished plate silica gel 60 F 254; elution agent: methylene chloride-methanol (8:1 v/v). RF value=0.31. $\lambda_{max}$ 510 nm, $\epsilon'=23.6$ cm$^2$ µmol$^{-1}$ (at pH 6) $\lambda_{max}$ 505 nm, $\epsilon'=33.3$ cm$^2$ µmol$^{-1}$ (at pH 8).

8.2. 2-(3,5-Di-tert.-butyl-4-hydroxyphenyl)-4-(4-bis-2,3-dihydroxypropyl)-aminophenyl]-5-methyl-1,3-oxazole from the compound of Example 3.3 and 2,3-epoxypropanol analogously to Example 8 (a). Title compound: yellowish oil; TLC silica gel plate 60; elution agent: dichloromethane-chloroform (8:1 v/v); RF value: 0.31 $\lambda_{max}$ 552 nm, $\epsilon'=30.3$ cm$^2$ µmol$^{-1}$.

EXAMPLE 9

2-(3,5-Dimethoxy-4-hydroxyphenyl)-4-[N-3-chloro-2-hydroxypropyl]-(aminophenyl)-5-methyl-1,3-oxazole 3.26 g. (0.01 mol) of the compound of Example 3 (free base) are heated under reflux for 6 hours in 65 ml. ethanol with 1.12 ml. (0.14 mol) epichlorohydrin, thereafter the reaction mixture is evaporated in a vacuum and the residue is stirred with 25 ml. water and thereafter with diethyl ether. There is obtained 1.6 g. (38.2% of theory) of colourless crystals of the title compound; m.p. 120°–123° C. (decomp.); $\lambda_{max}$ 554 nm, $\epsilon'=37.2$ cm$^2$ µmol$^{-2}$.

EXAMPLE 10

2-(3,5-Dimethoxy-4-hydroxyphenyl)-4-[N-3-morpholino-2-hydroxypropyl]-(aminophenyl)-5-methyl-1,3-oxazole 4.2 g. (0.01 mol) of the compound obtained in Example 9 are heated under reflux for 1.5 hours with 50 ml. morpholine. Thereafter, the reaction mixture is evaporated in a vacuum, the residue is stirred with acetone, the resultant morpholine hydrochloride is filtered off, this is washed with acetone and the filtrate is again evaporated. The residue, 8 g. of a brownish oil, is thereby purified chromatographically with silica gel 60 with isopropanol/n-butyl acetate/water (5/3/2 v/v/v). There is obtained 1.7 g. (36.4% of theory) of the title compound in the form of a honey-coloured oil. TLC: silica gel plate; elution agent: as in the column separation. RF value=0.51. $\lambda_{max}$ 551 nm, $\epsilon'=10$ cm$^2$ μmol$^{-1}$.

EXAMPLE 11

{{3-{4-[2-(3,5-dimethoxy-4-hydroxyphenyl)-5-methyl-4-1,3)-oxazolyl]-phenylamino}-2-hydroxypropyl}} phosphonic acid (a) Diethyl 2,3-epoxypropane phosphonate.

60 g. (0.44 mol) Epibromohydrin are mixed with 66.5 g. (68.6 ml.; 0.4 mol) triethyl phosphate and heated for 3 hours at 110° C. The resultant ethyl bromide is distilled off using a descending cooler and the crude product obtained is subsequently fractionally distilled. There are obtained 39.8 g. (51.2% of theory) of ester; b.p.$_{0.7}$ 93°–95° C. (GC 96.5%).

(b) Diethyl {{3-{4-[2-(3,5-dimethoxy-4-hydroxyphenyl)-5-methyl-4-(1,3)-oxazolyl-phenylamino-2-hydroxypropyl}}-phosphonate 3.26 g. (0.01 mol) of the compound of Example 3 (free base) are suspended in 100 ml. ethanol, 11.65 g. (0.06 mol) of the epoxide compound from step (a) above are added thereto and the reaction mixture is heated under reflux for 7 hours. After evaporating off the solvent, there is obtained a pale brown oil which is purified chromatographically on silica gel 60. Column: filling height 73 cm., elution agent: chloroform-methanol (19:1 v/v). Working up of the appropriate fraction gives 3.5 g. (67.3% of theory) of the pale yellow coloured title compound; m.p. 188° C. TLC finished plate: silica gel 60 F 254, elution agent: chloroform-methanol (8:1 v/v), RF value=0.313, $\lambda_{max}$ 517 nm, $\epsilon'=10.5$ cm$^2$ μmol$^{-2}$.

(c) {{3-{4-[2-(3,5-Dimethoxy-4-hydroxyphenyl)-5-methyl-4-(1,3)-oxazolyl]-phenylamino}-2-hydroxypropyl }}phosphonic acid hydrochloride 2.3 g. (0.044 mol) of the phosphonic acid ester of Example 11 (b) are heated under reflux for 3 hours with 25 ml. 6N hydrochloric acid and thereafter evaporated in a vacuum. The crude product obtained, 2.3 g. of semi-crystalline material, is stirred with 15 ml. isopropanol, filtered off with suction and dried. There is obtained 1.76 g. (88.8% of theory) of beige-coloured crystals of the title compound; m.p. 170°–182° C. (decomp.); $\lambda_{max}$ 583 nm, $\epsilon'=10.5$ cm$^2$ μmol$^{-1}$.

EXAMPLE 12

{{3-{4-[2-(3,5-Dimethoxy-4-hydroxyphenyl)]-5-methyl-4-(1,3)-oxazolylphenylmethylamino}-2-hydroxyphenyl}}phosphonic acid (a) Title compound: diethyl ester.

1 g. (1.9 mmol) of the compound of Example 11 (b) is hydrogenated in 100 ml. methanol with 0.1 g. platinum oxide in the presence of 0.5 ml. formaldehyde solution and 0.2 ml. concentrated hydrochloric acid for 4 hours at ambient temperature. After filtering off the catalyst with suction, the filtrate is evaporated in a vacuum. There is obtained 1.1 g. of reddish oil, which is purified chromatographically on a silica gel 60 column (4 cm. diameter, 70 cm. filling height). After evaporation of the appropriate fraction, there is obtained 0.31 g. (30.2% of theory) of amorphous, colourless powder. TLC finished plate: silica gel 60 F 254, elution agent: chloroform-methanol (19:1 v/v), RF value=0.34, $\lambda_{max}$ 589 nm, $\epsilon'=67.3$ cm$^2$ μmol$^{-1}$. (b) 0.3 g. (0.56 g. of the compound from Example 12 a) is heated under reflux in 10 ml. 6N hydrochloric acid for 2 hours, thereafter evaporated to dryness in a vacuum and the residue enriched with isopropanol. There are obtained 2.73 g. (57.1% of theory) of the title compound as a yellowish, amorphous powder. TLC finished plate: silica gel 60 F 254; elution agent: chloroform-methanol (19:1 v/v), RF value=0.26, $\lambda_{max}$ 593 nm, $\epsilon'=9.7$ cm$^2$ μmol$^{-1}$.

EXAMPLE 13

2-(3,5-Di-tert.-butyl-4-hydroxyphenyl)-4-{4-[N,N-bis(2,3-dihydroxypropyl)]-aminophenyl}-5-methyl-1,3-oxazole 3.8 g. (0.01 mol) 2-(3,5-di-tert.-butyl-4-hydroxyphenyl)-4-(4-aminophenyl)-5-methyl-1,3-oxazole (Example 3.3) are boiled under reflux for 8 hours with 3.7 g. (3.3 ml.; 0.05 mol) 2,3-epoxypropan-1-ol in 500 ml. ethanol. Thereafter, the reaction mixture is evaporated in a vacuum and the residue is purified column chromatographically. Column diameter 4.5 cm., filling height 70 cm., silica gel 60; elution agent: methylene chloride-methanol (8:1 v/v). By evaporation of the appropriate fractions, there are obtained 2.4 g. (45.6% of theory) of amorphous, light reddish powder. TLC finished plate: silica gel 60 F 254, elution agent: methylene chloride-chloroform (8:1 v/v), RF value =0.31, $\lambda_{max}$ 395 nm, $\epsilon'=22.2$ cm$^2$ μmol$^{-1}$.

EXAMPLE 14

N-{4-[2-(3,5-Di-tert.-butyl-4-hydroxyphenyl)-5-methyl-4-(1,3)-oxazolyl]-phenylamino}-acetic acid (a) Benzyl N-{4-[2-(3,5-di-tert.-butyl-4-hydroxyphenyl)-5-methyl-4-(1,3)-oxazolyl]-phenylamino}-acetate.

3.78 g. (0.01 mol) 2-(3,5-Di-tert.-butyl-4-hydroxyphenyl)-4-(4-aminophenyl)-5-methyl-1,3-oxazole are stirred under argon for 2.5 hours with 2.52 g. (0.011 mol) benzyl bromoacetate in 50 ml. anhydrous dimethylformamide in the presence of 2.36 g. (0.011 mol) 1,8-bis-dimethylaminonaphthalene, thereafter evaporated in a vacuum and the residue is taken up in 100 ml. methylene chloride, shaken up several times with water and the organic phase is dried with anhydrous sodium sulphate and evaporated. There are obtained 5.94 g. of a reddish, amorphous crude product which is purified column chromatographically. Column diameter 4.5 cm., filling height 85 cm., silica gel 60; elution agent: chloroform and 1% ethyl acetate. By evaporation of the appropriate fraction, there are obtained 3.11 g. (71.4% of theory) of the title compound as an amorphous, light reddish powder. TLC finished plate: silica gel 60 F 254, elution agent: chloroform and 1% ethyl acetate, RF value=0.29. (b) 2.3 g. (4.4 mol) of the above benzyl ester are dissolved in 100 ml. methanol and, after the addition of 0.2 g. palladium on active charcoal (10%), hydrogenated for 30 minutes at ambient temperature. After filtering off the catalyst with suction, the filtrate is evaporated in a vacuum to give 1.92 g. (98% of theory) of bright red, amorphous title compound. TLC finished plate: silica gel 60 F 254, elution agent: isopropanol-n-butyl acetate-water (5/3/2 v/v/v), RF value=0.53; $\lambda_{max}$ 510 nm, $\epsilon'=32.3$ cm$^2$ μmol$^{-1}$.

EXAMPLE 15

2-(3,5-Dimethoxy-4-hydroxyphenyl)-4-(4-dimethylaminophenyl)-1,3-thiazole (a) 2-(3,5-Dimethoxy-4-benzyloxyphenyl)-4-(4-dimethylaminophenyl)-1,3-thiazole.

3.7 g. (0.012 mol) 3,5-dimethoxy-4-benzyloxyphenyl-thioamide and 2.94 g. (0.012 mol) 4-dimethylamino-α- bromoacetophenone are heated under reflux for 3 hours in 120 ml. anhydrous ethanol. After cooling and placing in an ice bath, there are obtained 5.21 g. (97.3% of theory) of pale yellow crystals of the title compound; m.p. 205°–207° C. (decomp.). (b) The above-mentioned product is dissolved in 250 ml. methanol and hydrogen chloride passed into the boiling solution for 2 hours. After evaporating in a vacuum, the residue is dissolved in 150 ml. water and the thiazole liberated by the addition of ammonia. After taking up in dichloromethane and working up, there are obtained, after recrystallisation from ethanol, 3.1 g. (65.7% of theory) of the title compound as pale yellowish crystals; m.p. 219°–221° C. (decomp.), $\lambda_{max}$ 541 nm, $\epsilon' = 12.2$ cm$^2$ μmol$^{-1}$.

EXAMPLE 16

2-(3,5-Dimethoxy-4-hydroxyphenyl)-4,5-bis-(4-dimethylaminophenyl)-1,3-thiazole hydrochloride (a) 2-(3,5-Dimethoxy-4-benzyloxyphenyl)-4,5-bis-(4-dimethylaminophenyl)-1,3-thiazole.

5.68 g. (0.01 mol) of the title compound of Example 4 (c) are dissolved in 60 ml. anhydrous chloroform and, with the addition of 3.3 g. (0.015 mol) phosphorus pentasulphide, heated under reflux for 2 hours, while stirring. Thereafter, the reaction mixture is poured on to a mixture of ammonia and ice and the organic phase is separated off and shaken up several times with water. After drying and evaporating, one obtains 5.8 g. of the title compound 16 (a) as a brown oil. TLC silica gel plate 60, elution agent: ethyl acetate, RF value=0.88. (b) The above-mentioned product is heated under reflux for 30 hours with 30 ml. 6N hydrochloric acid, after the addition of ammonia extracted 3 times with 30 ml. amounts of dichloromethane, worked up and purified column chromatographically on silica gel. Elution agent: methanol/chloroform (6/1 v/v). The appropriate fractions contain 2.2 g. (46.2% of theory) of the title compound; yellowish crystals; m.p. 218° C. (decomp.); $\lambda_{max}$ 552 nm, $\epsilon' = 10.8$ cm$^2$ μmol$^{-1}$.

EXAMPLE 17

Survey of the optical properties of compounds of general formula (I)

The following procedure is used for determining the molar extinction coefficients: $2 \times 10^{-2}$ mol of indicator of general formula (I) are dissolved in 100 ml. 0.1M hydrochloric acid. If the compound does not dissolve quantitatively, then it is dissolved in a mixture of hydrochloric acid/methanol (9:1 v/v). 0.1 ml. of this solution are diluted with 10 ml. 0.1M phosphate buffer (pH 6.0). 10 μl. of the indicator solution thus obtained are pipetted into a mixture consisting of 10 μl diluted. hydrogen peroxide solution (100 μl. 30% hydrogen peroxide are diluted with water to 100 ml.), 10 μl peroxidase solution (600 U peroxidase are dissolved in 1 ml. water) and 10 ml. 0.1M phosphate buffer (pH 6.0). The indicator is oxidised and the solution becomes coloured. After 60 seconds, a spectrum is recorded of the coloured solution and from the extinction values there are calculated the molar extinction coefficients (if the coloured material formed precipitates out, then a mixture of buffer, acetone or methanol (9:1 v/v) is used).

According to the same process, the hydrogen peroxide concentrations can be determined from samples or the concentrations of substrates from which hydrogen peroxide results as reaction product by a preceding enzymatic reaction.

EXAMPLE 18

Test system for the detection of uric acid in aqueous solutions

On to a polyester film precoated with gelatine there is poured, with a wet film thickness of 300μ, a gelatine matrix of the composition given hereinafter and subsequently dried. Into 47.5 ml. trisphosphate buffer (0.5M, pH 7.2) are introduced 8.4 g. gelatine, 0.25 g. Tween 20, 0.5 kU uricase, 5 kU peroxidase and 100 mg. indicator substance of Example 3 (2-(3,5-dimethoxy-4-hydroxyphenyl)-4-(4-aminophenyl)-5-methyl-1,3-oxazole hydrochloride). The reagent film so produced is worked up to give a test system corresponding to FIG. 1 of the accompanying drawings. 35 μl. uric acid solution are applied to the dosing zone. By pressing the reagent zone and the fabric on to the transport zone, the reaction is started. After 2 minutes, measurement is made in a remission photometer (the fabric has the function of equalizing the unevennesses of the glass fibre fleece).

The calibration curve obtained with the abovedescribed system is given in the following Table:

| uric acid concentration | % remission |
| --- | --- |
| 3 mg./dl. | 54.9 |
| 5 mg./dl. | 48.8 |
| 7 mg./dl. | 43.2 |
| 9 mg./dl. | 38.7 |
| 11 mg./dl. | 33.6 |
| 14 mg./dl. | 30.9 |

EXAMPLE 19

Test system for the detection of creatinine in serum

An absorbent paper (stencil paper of the firm Schöller & Hösch, surface weight 12 g./m$^2$; absorbency 50 ml./m$^2$) is impregnated with a solution of 200 kU peroxidase and 1.2 g. collagen hydrolysate dissolved in 100 ml. phosphate buffer (0.1M, pH 8.0) and dried. In a second impregnation step, the pre-impregnated paper is post-impregnated with a solution consisting of 2 mmol indicator substance of Example 8 (a) (2-(3,5-dimethoxy-4-hydroxyphenyl)-4-[4-bis-(2,3-dihydroxypropyl)-aminophenyl]-5-methyl-1,2-oxazole) in 100 ml. methanol and dried. Reagent paper (a) is thus obtained.

For the production of reagent paper (b), the abovementioned carrier is impregnated with a solution of 5 kU sarcosine oxidase, 30 kU creatinine amidohydrolase, 40 kU creatinine amidinohydrolase and 0.5 g. Triton×100 in 100 ml. 0.1M phosphate buffer (pH 8.0) and dried.

Both papers are incorporated into a test system according to FIG. 2 of the accompanying drawings.

For the detection of creatinine in serum, 30 μl. of serum are pipetted on to the dosing zone. The reaction is started by pressing the enzyme and indicator paper on to the transport zone. After one minute, the colour formed is measured remission photometrically. Evaluation takes place by means of a calibration curve.

The following Table gives the values for a calibration curve for creatinine in serum.

| creatinine concentration | % remission |
| --- | --- |
| 0.1 mg./dl. | 68.1 |

-continued

| creatinine concentration | % remission |
| --- | --- |
| 0.5 mg./dl. | 59.9 |
| 1.5 mg./dl. | 48.2 |
| 5.0 mg./dl. | 35.0 |
| 10.0 mg./dl. | 30.7 |

EXAMPLE 20

Test system for the detection of uric acid in blood

From the components set out hereinafter, there is prepared a coating mass and this is raked out with a wet film thickness of 200μ on to a transparent film and then dried. 18 g. of a synthetic resin dispersion of a mixed polymer of vinyl acetate and vinyl propionate, 1.5 g. of alginate, 68 ml. of 0.5M tris-citrate buffer (pH 7.5), 0.7 g. of the indicator substance according to Example 3, 2 kU uricase, 100 kU peroxidase, 0.5 g. Triton×100 and 12 g. diatomaceous earth are stirred until homogeneous.

On to the layer so produced, there is raked on a second layer as optical, white background, which has the composition given hereinafter, with a layer thickness of 200μ and dried. 52 ml. 0.1M tris-citrate buffer (pH 7.0), 5.5 g. titanium dioxide, 2.7 g. diatomaceous earth, 0.4 g. alginate, 1.4 g. of a synthetic resin dispersion of a mixed polymer of vinyl acetate and vinyl propionate and 0.2 g. Triton×100.

The test film thus produced is worked up to give tests according to FIG. 3 of the accompanying drawings.

For the detection of uric acid in blood, 30 μl. of blood are applied to the dosing zone, after one minute pressure is applied in the reagent flap and after a further 2 minutes the colour formed is measured with a remission photometer and the uric acid value determined from a previously produced calibration curve.

The following Table gives the values for a calibration curve:

| uric acid concentration | % remission |
| --- | --- |
| 4.6 mg./dl. | 58.0 |
| 6.0 mg./dl. | 50.6 |
| 7.9 mg./dl. | 43.1 |
| 9.0 mg./dl. | 40.5 |
| 10.6 mg./dl. | 36.1 |
| 13.5 mg./dl. | 31.8 |
| 15.6 mg./dl. | 28.7 |

EXAMPLE 21

Test system for the detection of GPT in blood

Absorbent papers (stencil papers of the firm Schöller & Hösch, surface weight 12 g./m³; absorbency 50 ml./m²) are impregnated with one of the solutions 1 and 2 described hereinafter and then dried.

Solution 1

In one liter of a 0.2M buffer of potassium hydroxide solution and 2-(N-morpholino)-ethanesulphonic acid of pH 6.7 are dissolved 0.03 mol α-ketoglutarate, 0.8 mol alanine, 0.01 mol magnesium chloride, 0.0001 mol ascorbic acid, 0.009 mol of the substance of Example 7, i.e. 2-(3,5-dimethoxy-4-hydroxyphenyl)-4-(dimethylamino-phenyl)-5-methyl-1,3-oxazole hydrochloride, and 5 g. octyl pyranoside. This is used to produce reagent paper (a).

Solution 2

In one liter of the above-described buffer are dissolved 0.003 mol thiamine pyrophosphate, 500 kU pyruvate kinase, 500 kU peroxidase and 100 kU ascorbate oxidase. This is used to produce reagent paper (b).

These reagent papers are worked up to give a test system according to FIG. 2 of the accompanying drawings.

For the determination of the enzyme activity, 30 μl. of blood are pipetted on to the dosing zone, after 1 minute the covering film and the reaction papers are pressed together and the colour development is followed with a remission photometer. Evaluation takes place via a two point measurement from a reference curve. The reference curve is produced by making a series of dilutions with enzyme activities of from 10 to 1000 U/liter and the remission values determined via fixed time measurements in a remission photometer.

EXAMPLE 22

Process for the detection of glucose concentrations in blood for the diagnosis of hypoglycaemia A raw film mass is produced in the following manner: 10 g. of 1.7% alginate swelling in a 0.5M phosphate buffer (pH 5.0), 15 g. aqueous synthetic dispersion of a co-polymer of vinyl acetate and vinyl propionate, 5 g. of a 15% aqueous solution of 4-dodecylbenzenesulphonate, 25 kU glucose oxidase, 200 kU peroxidase, 270 mg. of substance according to Example 3, 10 g. diatomaceous earth and 0.4 ml. hexanol are stirred up to give a homogeneous slurry and this is then raked with a wet film thickness of 150μ on to a multifilar fabric (2 F/964 of the firm Schwiezer Seidengaze Fabrik) and subsequently dried.

This film is worked up to give a test system according to FIG. 4 of the accompanying drawings. For the determination of glucose, 30 μl. of blood are pipetted on to the dosing zone, the covering film and the reagent film are pressed on to the transport zone and the resulting reaction colour is measured with a remission photometer. The glucose concentrations are determined on the basis of a calibration curve which has the following appearance:

| mg. glucose/dl. | % remission |
| --- | --- |
| 20 | 37.2 |
| 40 | 22.6 |
| 60 | 18.6 |
| 80 | 12.8 |

List of references:

1. reagent zone carrier (transparent)
2. reagent zone
3. fabric
4. transport zone of glass fibres
5. separation zone of glass fibres
6. fixing fabric
7. covering film (transparent)
8. reagent paper (a)
9. reagent paper (b)
10. optically white background (porous)
11. multifilar fabric
12. carrier foil
13. point of adhesion.

It will be understood that the specification and examples are illustrative but not limitative of the present invention and that other embodiments within the spirit and scope of the invention will suggest themselves to those skilled in the art.

What is claimed is:

1. A compound of the formula

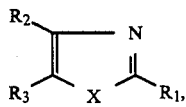 (I)

wherein

X is oxygen or sulphur;

$R_1$ is julolidine, tetrahydroquinoline or tetrahydroquinoline with substituted or unsubstituted $C_1$–$C_6$ alkyl on the nitrogen atom, the substituents being a sulfo phosphonic acid or carboxylic acid residue, or $R_1$ is a group of the formula

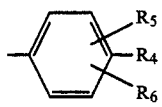

wherein $R_4$ is hydroxyl or mono-or dialkylated amino wherein each alkyl contains up to 6 carbon atoms and is unsubstituted or substituted one or more times by a hydroxyl, alkoxy, halogen, morpholine, or a sulfo, carboxylic acid or phosphonic acid residue, which acid residue is optionally esterified, $R_5$ and $R_6$, which can be the same or different, are hydrogen, $C_1$–$C_6$ alkyl, $C_1$–$C_6$ alkoxy or $C_1$–$C_6$ alkyl substituted one or more times by halogen, hydroxyl, methoxy, carboxy, a morpholino radical, a sulfo or a phosphonic acid residue, which can also be esterified by methanol or ethanol, or $C_1$–$C_6$ alkoxy substituted by a carboxyl group, $R_2$ is hydrogen, $C_1$–$C_6$ alkyl, or $C_1$–$C_6$ alkyl, substituted one or more times by halogen, hydroxyl, methoxy, carboxy, a morpholino radical, a sulfo acid or a phosphonic acid residue, which can also be esterified by methanol or ethanol, or $C_1$–$C_6$ alkoxy substituted by a carboxyl group, or is julolidine, tetrahydroquinoline or tetrahydroquinoline substituted with substituted or unsubstituted $C_1$–$C_6$ alkyl on the nitrogen atom, the substituents being a sulfo, phosphonic acid or carboxylic acid residue, or is a group of the formula:

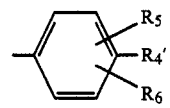

wherein $R_5$ and $R_6$ have the same meanings as above and $R'_4$ is hydroxyl, amino, or mono- or dialkylated amino wherein the alkyl groups contain up to 6 carbon atoms and are unsubstituted or substituted one or more times by a hydroxyl, alkoxy, halogen, morpholine, or a sulfo, carboxylic acid or phosphonic acid residue, which acid residue is optionally esterified; and $R_3$ has the same meaning as $R_2$ or is $C_1$–$C_6$ alkoxy, dialkylamino with up to 6 carbon atoms in each alkyl or phenyl, or is cycloalkyl with 3 to 7 carbon atoms, phenyl or pyridyl, and wherein at least one of the residues $R^2$ and $R^3$ is julolidine, tetrahydroquinoline or tetrahydroquinoline substituted with substituted or unsubstituted $C_1$–$C_6$ alkyl on the nitrogen atom, the substituents being a sulfo, phosphonic acid or carboxylic acid residue, or is a group of the formula:

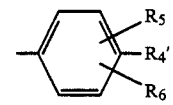

wherein $R'_4$, $R_5$, $R_6$ have the same meanings as above and wherein at least one of the substituents $R_4$ and $R'_4$ is hydroxyl and the salts thereof.

2. A reagent for the detection of hydrogen peroxide or of peroxidate-active substances, consisting of the compound of claim 1 and conventional active and adjuvant substances.

3. The reagent of claim 2 in the form of tablets, lyophilisates, impregnated reagent carriers or reagent films.

4. The compound of claim 1 consisting of 2-(3,5-dimethoxy-4-hydroxyphenyl)-4-(4-aminophenyl)-5-methyl-1,3-oxazole hydrochloride.

5. The compound of claim 1 consisting of 2-(3,5 Dimethoxy-4-hydroxyphenyl)-4-(4-dimethylaminophenyl)-5-methyl-1,3-oxazole hydrochloride.

6. The compound of claim 1 consisting of 2-(3,5-Di-tert.-butyl-4-hydroxyphenyl)-4-(4-dimethylaminophenyl-5-methyl-1,3-oxazole.

7. The compound of claim 1 consisting of 2-(3,5-di-tert.-butyl-4-hydroxyphenyl)-4-(4-aminophenyl)-5-methyl-1,3-oxazole hydrochloride.

* * * * *

UNITED STATES PATENT AND TRADEMARK OFFICE
CERTIFICATE OF CORRECTION

PATENT NO. : 4,966,855

DATED : October 30, 1990

INVENTOR(S) : Deneke et al.

Page 1 of 2

It is certified that error appears in the above-identified patent and that said Letters Patent is hereby corrected as shown below:

Change

Col. 3, line 34:  "dimathylaminophenyl" to -- dimethylaminophenyl --.

Col. 7, line 59:  change "2-(3,5-" to -- 7.  2-(3,5-  --.

Col. 8, line 57:  change "4-4-(N-2,3-" to -- 4-[4-(N-2,3-  --.

Col. 8, line 60:  change "4-4-(N-2,3-" to -- 4-[4-(N-2,3-  --.

Col. 8, line 58:  change "aminophenyl-5" to -- aminophenyl]-5 --.

Col. 8, line 61:  change "methylaminophenyl-5" to -- methylaminophenyl]-5 --.

Col. 9, line 2:   change "ethanesulch-onic" to -- ethanesulphonic --.

Col. 9, line 13:  change "54-methyl" to -- 5-methyl --.

Col. 9, line 16:  change "54-methyl" to -- 5-methyl --.

Col. 9, line 18:  change "54-methyl" to -- 5-methyl --.

Col. 9, line 14:  change "(1,3)" to -- 4-(1,3) --.

Col. 9, line 17:  change "(1,3)" to -- 4-(1,3) --

Col. 9, line 19:  change "(1,3)" to -- 4-(1,3) --.

UNITED STATES PATENT AND TRADEMARK OFFICE
CERTIFICATE OF CORRECTION

PATENT NO. : 4,966,855
DATED : October 30, 1990
INVENTOR(S) : Deneke et al.

It is certified that error appears in the above-identified patent and that said Letters Patent is hereby corrected as shown below:

Col. 9, line 51:  change "-{5-[2" to -- 1-{5-[2 --.

Col. 11, line 29: change "(55%" to -- (55.6% --.

Col. 12, line 34: change "$\mu mol^{1}$" to -- $\mu mol^{-1}$ --.

Col. 14, line 20: change "80%" to -- 80.2% --.

Col. 14, line 52: change "$\eta mol^{-1}$" to -- $\mu mol^{-1}$ --.

Col. 17, line 42: change "$mol^{-1}$" to -- $\mu mol^{-1}$ --.

Col. 15, line 49: change "84%" to -- 84.6% --.

Signed and Sealed this

Seventeenth Day of November, 1992

Attest:

DOUGLAS B. COMER

*Attesting Officer*    *Acting Commissioner of Patents and Trademarks*